United States Patent [19]
Errico et al.

[11] Patent Number: 5,653,763
[45] Date of Patent: Aug. 5, 1997

[54] INTERVERTEBRAL SPACE SHAPE CONFORMING CAGE DEVICE

[75] Inventors: Joseph P. Errico, Far Hills; Thomas J. Errico, Summit, both of N.J.

[73] Assignee: Fastenetix, L.L.C., Summit, N.J.

[21] Appl. No.: 622,891

[22] Filed: Mar. 29, 1996

[51] Int. Cl.⁶ ..................................................... A61F 2/44
[52] U.S. Cl. .................. 623/17; 623/16; 606/61; 411/55
[58] Field of Search ...................... 411/49, 55, 57, 411/71; 623/16, 17, 18; 606/60, 61, 63, 73

[56] References Cited

U.S. PATENT DOCUMENTS 5,554,191 9/1996 Lahille et al. ..................... 623/17

*Primary Examiner*—John G. Weiss
*Assistant Examiner*—Francis K. Cuddihy
*Attorney, Agent, or Firm*—Joseph P. Errico

[57] ABSTRACT

An orthopaedic cage device having a rectangular cross-section and an intervertebral space shape conforming structure is formed of two opposing shell elements being hinged at one end to form an interior volume therebetween. The surface of the interior volume is tapered in the axial direction. A threaded shaft is axially disposed in the interior volume and is held in place by a retaining ring slideably mounted at the non-hinged axial end of the device. A nut, being of substantially the same dimension as the maximum cross-section of the interior volume in its initial disposition, is disposed on the threaded shaft such that rotation of the shaft causes the nut to translate axially within the interior volume. This translation causes the nut to engage the tapered surface of the interior volume, which in turn causes the non-hinged end of the device to spread such that the device conforms to the natural space between the vertebral bones and provides for the proper curvature of the spine.

9 Claims, 9 Drawing Sheets

INTERVERTEBRAL SPACE SHAPE CONFORMING CAGE DEVICE

BACKGROUND OF THE INVENTION

1. Field of the Invention

This invention relates generally to a spinal implant assembly for anterior implantation between adjacent vertebral bones to potentiate fusion, and more particularly to an implantable device which conforms to the natural curvature of the spinal column.

2. Description of the Prior Art

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height, however, they do have specific drawbacks which limit their effectiveness. First among these drawbacks is that the devices, once implanted, do not permit the spine to retain its original and proper curvature. Causing a fusion to grow and immobilize the spine at a curvature which is not natural can cause discomfort and potentially damaging effects.

A second concern with respect to cylindrical implants of this type is that there will be a tendency for the devices to roll and/or slide. Such undesirable motion by the implant can cause loosening, or worse, complete dislocation from its proper position.

It is, therefore, an object of the present invention to provide a new and novel vertebral/intervertebral spacer which conforms to the natural curvature of the patient's spine.

It is further an object of the present invention to minimize the risk of dislocation by providing a geometric shape which is more suitable for stable positioning than cylindrical implants.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a shape conforming cage device having a rectangular cross-section. In a first embodiment the device comprises a pair of cupping opposing elements, which are hinged together at an axially distal end, and a threaded shaft and nut mounted between the elements whereby rotation of the shaft causes the nut to translate along the shaft thereby effecting a spreading of the elements at the other end (expanding the device at the unhinged, proximal end).

More specifically, the device comprises a pair of shell-like cupping elements which are hinged together at one end, defining an interior volume therebetween. The top and bottom surfaces of the hinged structure are planar, and are initially disposed in parallel. The top and bottom interior surfaces of the cupping elements are axially tapered relative to the corresponding exterior surfaces such that, in the initial disposition, the interior volume is wider at the hinged end than at the unhinged (and open) proximal end. A shaft having a threaded portion is axially positioned between the opposing elements, such that the head of the shaft may be engaged by a screwdriving tool through the open proximal end. A nut is positioned on the shaft such that its outer surface contacts the interior surfaces of the opposing elements and may translate along the shaft via rotation of the shaft. In the initial disposition, the nut is positioned at the distal end of the shaft which is closest to the hinge, such that the exterior surfaces may remain in parallel. As the shaft is rotated, the nut translates along the shaft toward the proximal end, causing the opposing elements to expand as the nut engages and spreads the tapering of the inner surfaces, thereby widening the interior volume.

The shaft is held in place between the opposing cupping elements by the nut and by a retaining ring disposed between the upper and lower interior surfaces at the proximal end of the device (recessed slightly from the opening). The retaining ring includes a pair of posts extending radially outward from the ring in diametrically opposite directions, which posts extend upwardly and downwardly into the interior surfaces of the corresponding opposing elements. The posts are slidably retained within the opposing elements such that the posts do not interfere with the expansion of the elements as the nut translates within the interior volume.

In a preferred embodiment, the lateral sides of the cupping elements are constructed with a groove and tooth conformation so as to ensure stability of the device during expansion.

During the implantation procedure, the surgeon first removes the degenerated disc material from between the vertebral bodies and then prepares the adjacent exposed bone surfaces for the introduction of a pair of devices. Each device is properly positioned spaced apart from one another, each being inserted transverse to the axis of the spine, with its hinged distal end directed posteriorly, and its proximal open end directed anteriorly. The threaded shafts are then engaged to cause the corresponding nuts to translate anteriorly thereby causing the proximal end of the device to open, pushing the exterior surfaces of the opposing elements into full and flush contact the exposed surfaces of the adjacent bones. This expansion allows the device to conform to the proper contour and shape of the specific patient's spine, or the natural curvature at the level of the spine where the surgery is taking place. The space between the devices is clear for bone graft material and/or bone growth enhancing materials to be inserted to potentiate the growth of a solid bone bridge across the intervertebral space.

In an alternative embodiment, the direction of the taper of the interior surfaces of the opposing cupping elements, and the corresponding direction of axial translation of the nut may be reversed so that the movement of the nut toward the distal, hinged, end causes the proximal end to expand.

In another embodiment, a plurality of nut and shaft expansion means (either the distally or proximally directed ones) may be included in one device so that only a single device need be implanted. In such a device, the opposing cupping elements preferably include holes, or one hole, through which bone may grow across the intervertebral space.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
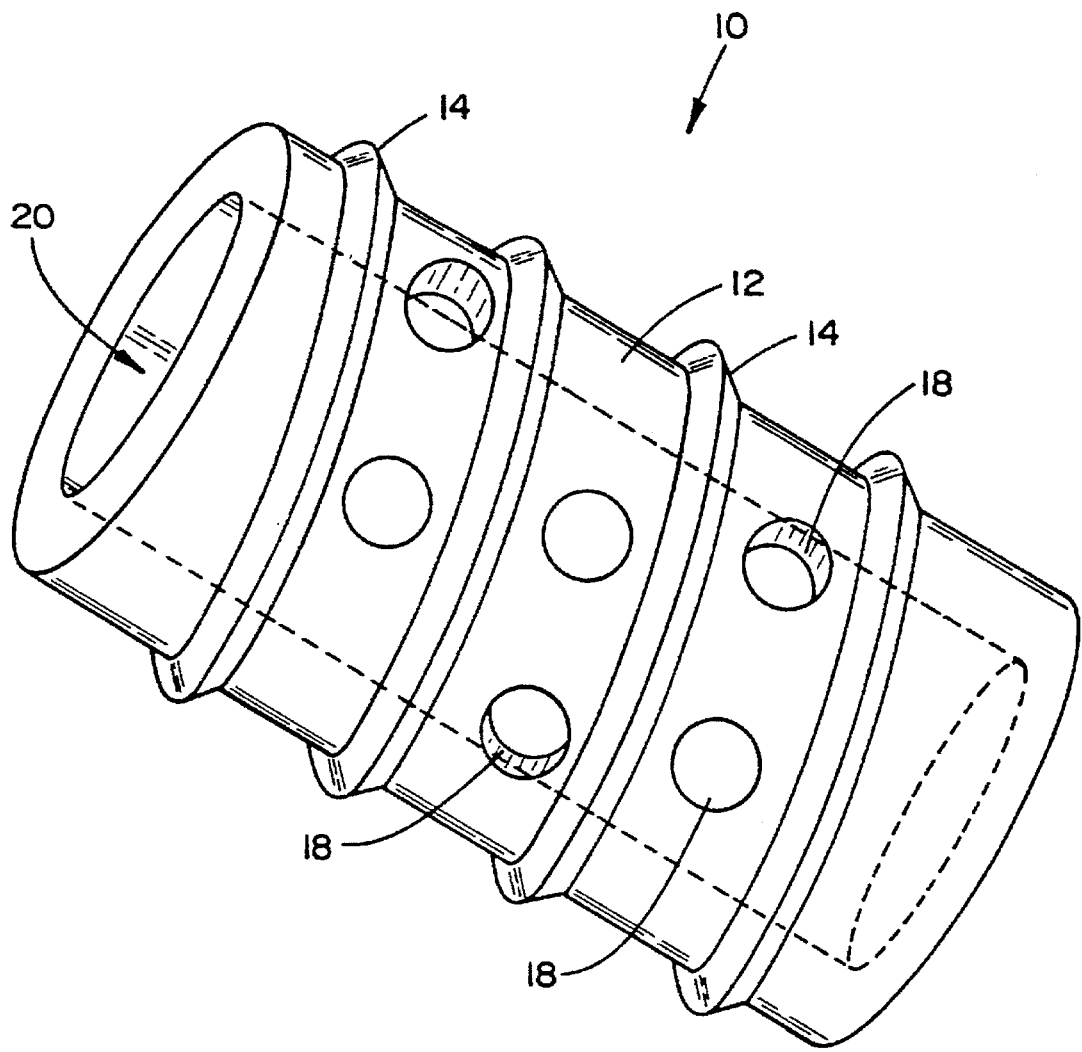
FIG. 1 is a side perspective view of an intervertebral spacer of the prior art.
Figure 2:
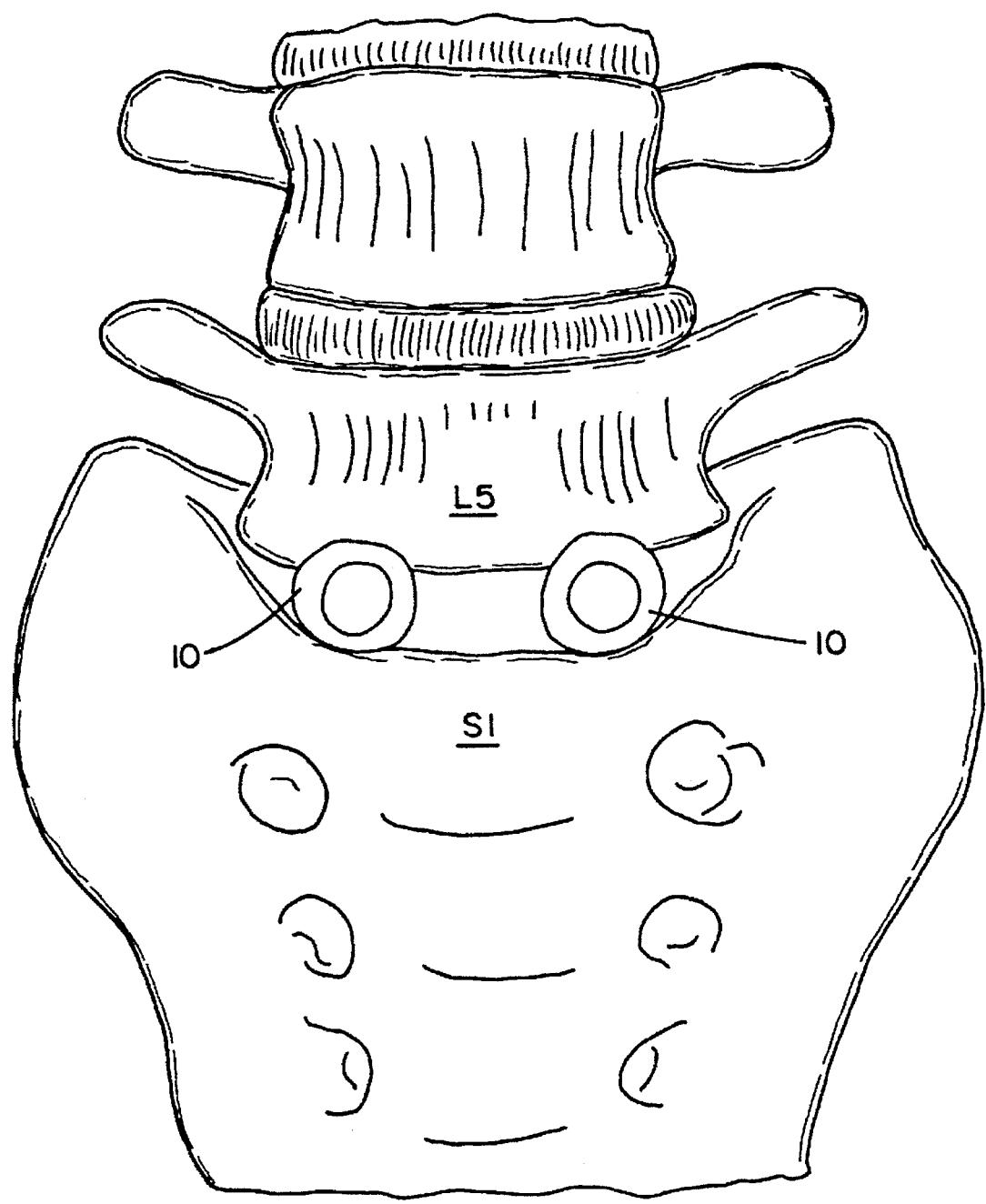
FIG. 2 is a front view of the anterior portion of the lumbo-sacral region of a human spine, into which a pair of intervertebral spacers of the type shown in FIG. 1 have been implanted.
Figure 3:
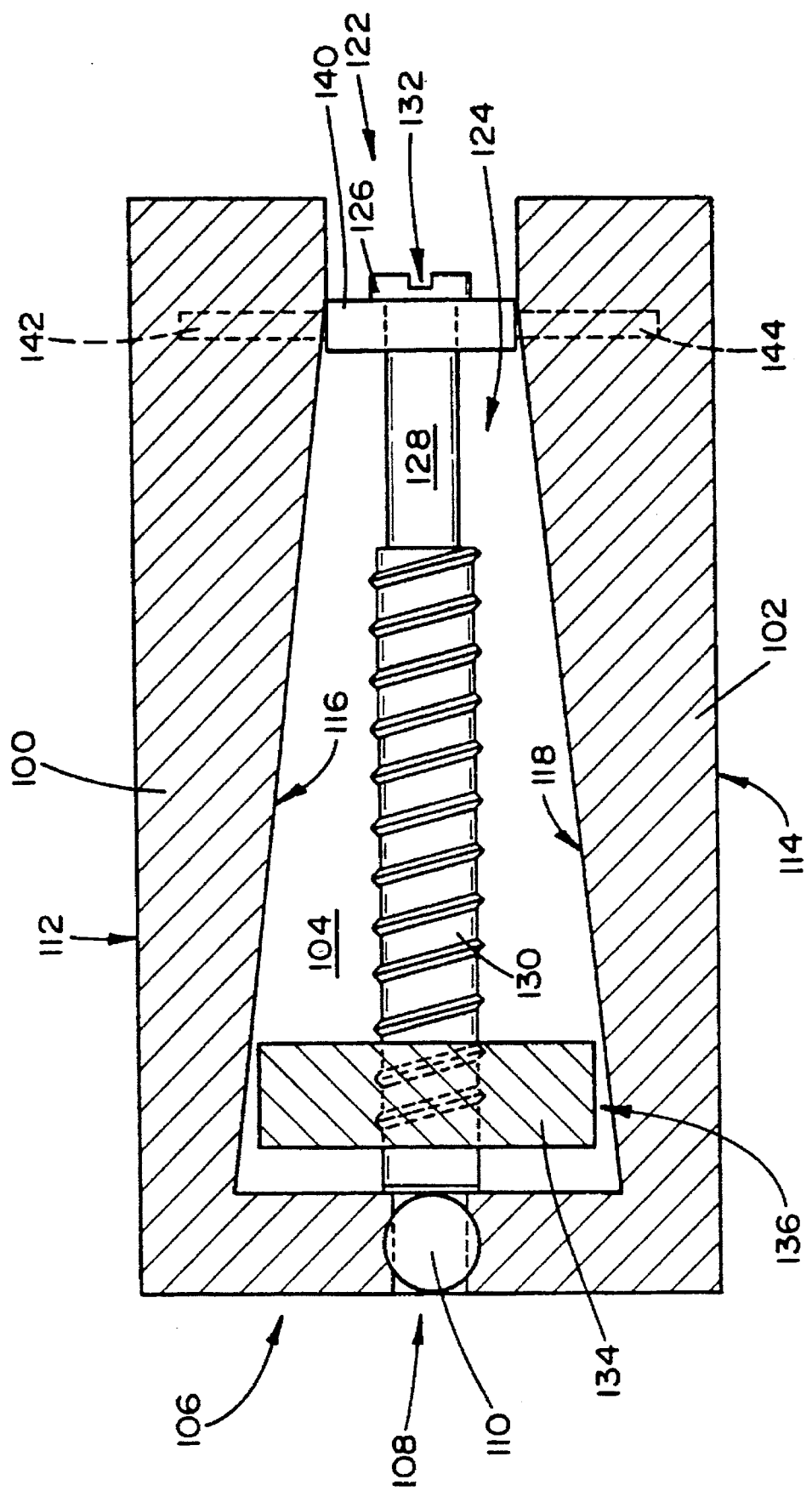
FIG. 3 is a side cross-section view of a one aspect of the present invention.

Referring now to FIG. 3 a side cross-section view of a first embodiment of the present invention is shown. The invention is a shape conforming cage device comprising a pair of opposing shell-like cupping structural elements 100,102, having their concave surfaces facing such that an interior volume 104 is defined therebetween. The elements 100,102 are hinged together at an axially distal end 106; the hinge 108 comprising mutually interlocking hinge-post receiving channels (see FIG. 4) having a hinge-post 110 inserted therethrough, about which the two cupping elements 100, 102 rotate.

The top and bottom surfaces 112 and 114, respectively, of the hinged structure are planar (and may include a roughened surface conformation so as to best grip the bone against which it is implanted), and are initially disposed in parallel. The top and bottom interior surfaces 116 and 118, respectively, of the shell-like cupping elements 100,102 include an axial taper relative to the corresponding exterior surfaces 112,114 such that, in the initial disposition, the interior volume 104 is wider at the hinged end 106 than at the unhinged (and open) proximal end 122.

A shaft 124 is axially positioned between the opposing elements 100,102. The shaft 124 comprises a head 126, a neck portion 128 having a narrower diameter than the head 126, and a threaded portion 130 extending from the neck 128. The head 126 of the shaft 124 includes a slot 132 so that it may be engaged by a screwdriving tool through the open proximal end 122 between the elements 100,102. (It shall be understood that numerous alternate designs for the head 126 may be substituted for engagement with and rotation of the shaft 124, all of such alternatives being functional equivalents fully anticipated by the scope of the present invention.)

A nut 134 is positioned on the threaded portion 130 of the shaft 124 such that its outer edge 136 abuts the interior surfaces 116,118 of the opposing elements 100,102, such abutment preventing the nut 134 from rotation along with the shaft 124 when it is manipulated. Instead, the nut 134 translates along the shaft 124 via rotation thereof, the direction of translation corresponding to the direction of the threading and the rotation. In the initial disposition, the nut 134 is positioned at the end of the shaft 124 which is closest to the hinged end 106, such that the exterior surfaces 112,114 remain parallel. As the shaft 124 is rotated, the nut 134 translates along the threaded portion 130 toward the proximal end 122, causing the opposing elements 100,102 to expand as the nut 134 engages the tapering of the inner surfaces 116,118, thereby widening the interior volume 104.

The shaft 124 is held in place between the opposing cupping elements 100,102 at the distal end 106 thereof by the nut 134, and at the proximal end 122 by a retaining ring 140 disposed between the upper and lower interior surfaces 116,118 at the proximal end 122 of the device (recessed slightly from the opening). The retaining ring 140 includes a pair of posts 142,144 extending radially outward at diametrically opposite positions. The posts 142,144 extend upwardly and downwardly, respectively, through the corresponding interior surfaces 116,118 of the opposing elements 100,102 into holes formed therein for slideably receiving the posts. The posts 142,144 are slideably retained such that they do not interfere with the expansion of the elements 100,102 as the nut 134 translates along the threaded portion 130 of the shaft 124 within the interior volume 104.

It shall be understood that the diameter of the hole in the retaining ring 140, through which the shaft 124 is disposed, is sized to permit the unthreaded narrow neck portion 128 to slide freely, but to block both the head 126 and the threaded portion 130 from passing through.

Figure 4:
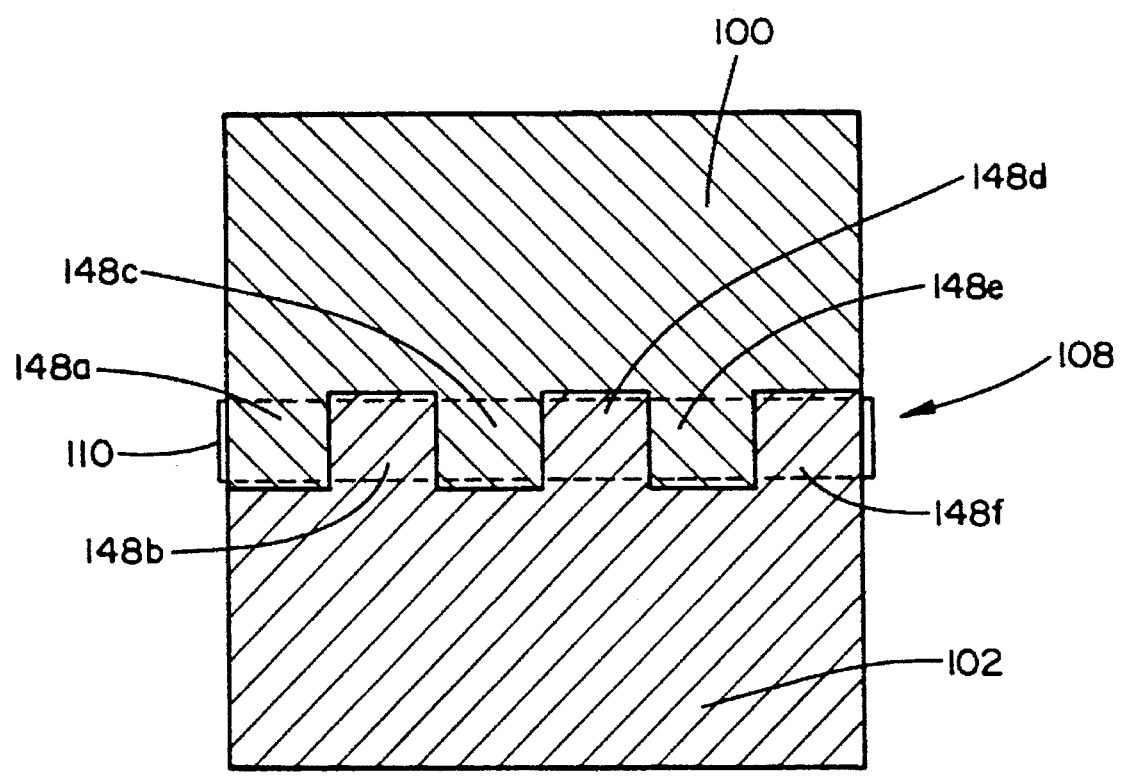
FIG. 4 is a rear perspective view of the hinged end of one aspect of the present invention.
Figure 5:
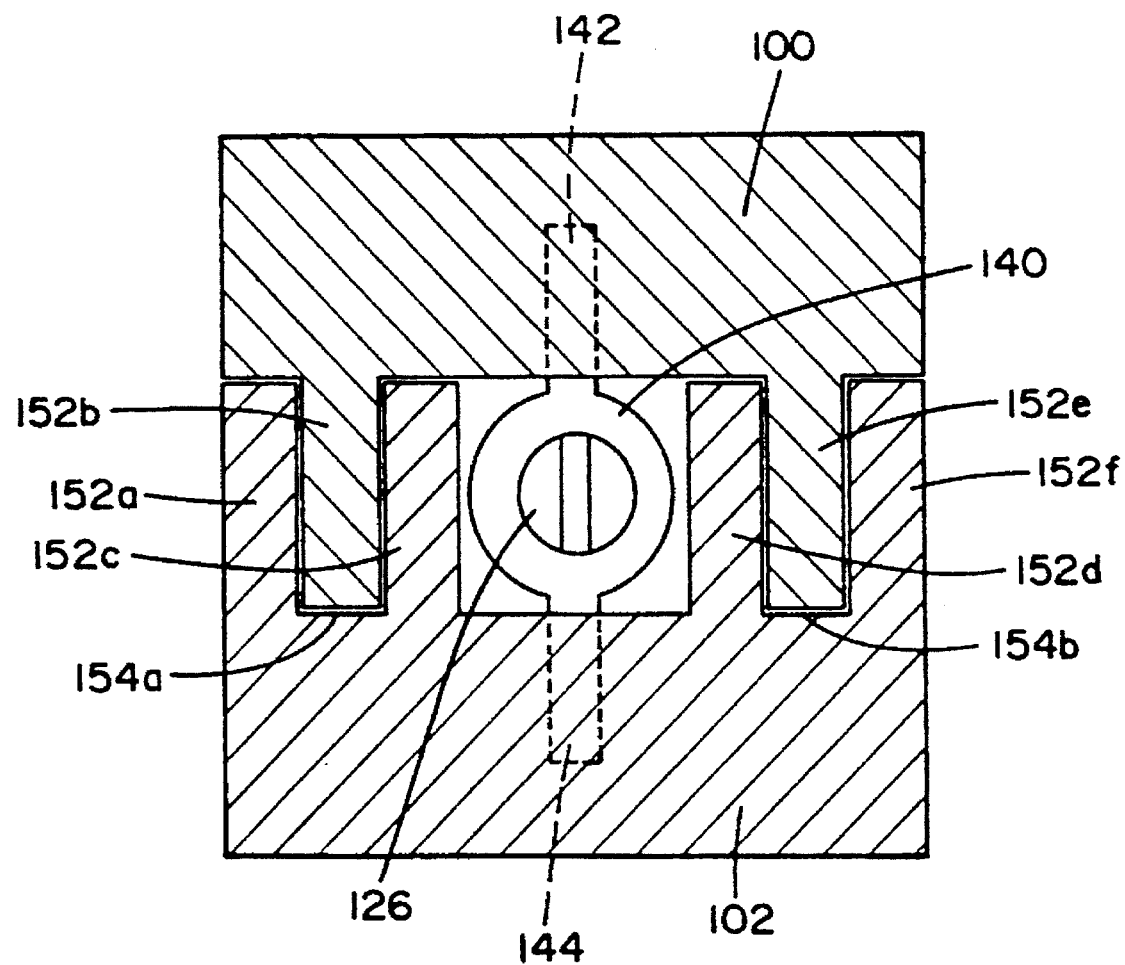
FIG. 5 is a front perspective view of one aspect of the present invention.

Referring now to FIGS. 4 and 5, in which rear and front end views of the embodiment of the present invention, which was set forth herein above with respect to FIG. 3 are shown, the functioning of the hinge 108 and lateral stabilizing features of the device are shown. More particularly, with respect to the hinge 108, each of the opposing shell-like cupping elements 100,102 include interlocking hinge-post receiving channels 148a–f, through which a hinge-post 110 is inserted. The opposing elements 100,102 are thereby swingably coupled.

With respect to the lateral stabilizing features of the present invention, shown here in FIG. 5, the opposing elements 100,102 include interlocking teeth and grooves 152a–f, 154a–b, which permit unidirectional relative movement of the opposing elements 100,102. While the posts 142,144 of the retaining ring 140, and their disposition within the opposing elements 100,102 provide some lateral stability, these additional laterally stabilizing features are important for ensuring the long term viability of the implant. It is understood that a variety of other structural conformations, some being similarly mutually engaging, as well as alternative means for restricting possible motion to unidirectionality, may be substituted for the teeth and groove design described herein. Such equivalents are fully anticipated by the present invention, the scope of which shall not be limited by such features.

Figure 6:
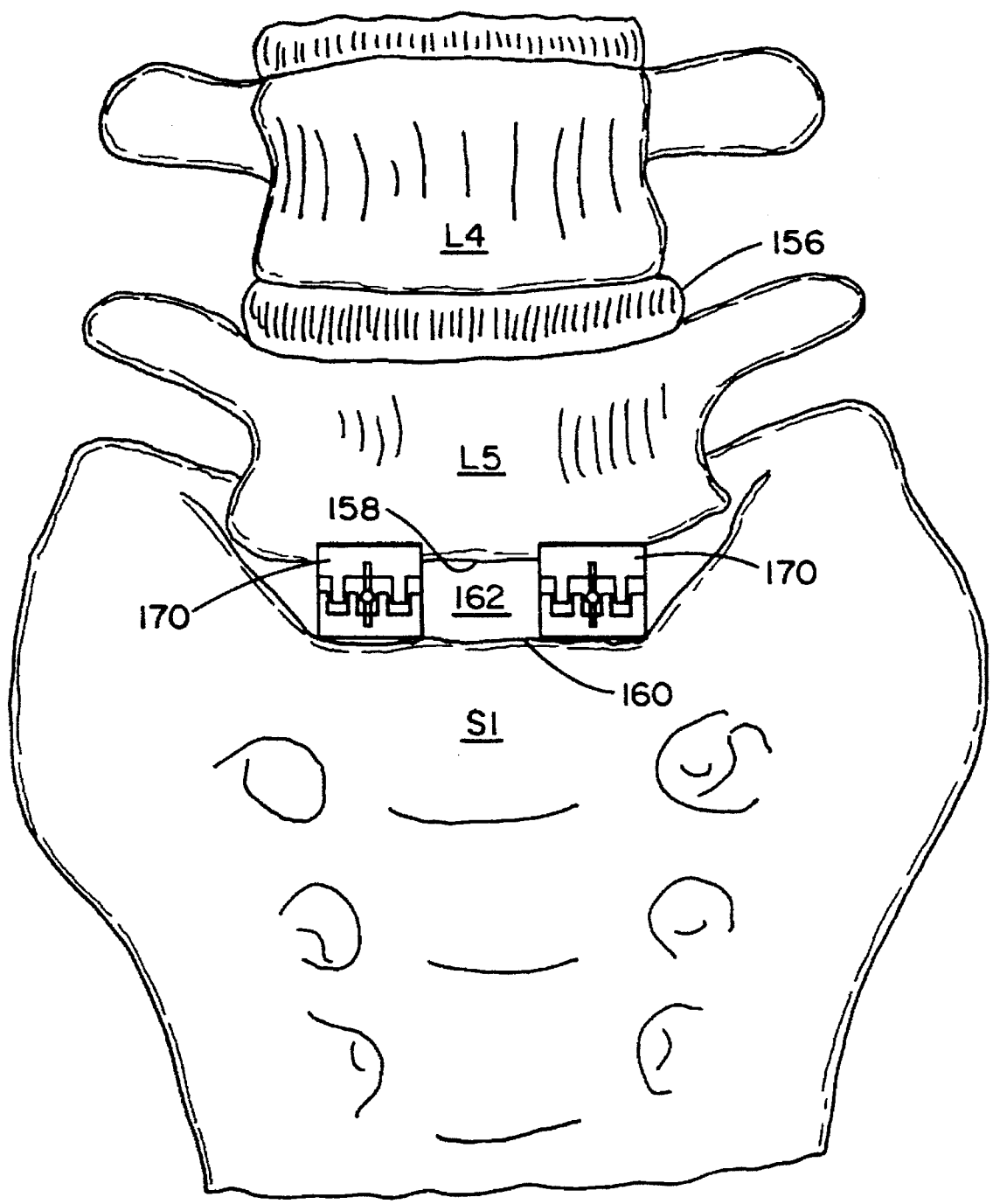
FIG. 6 is a front view of the anterior portion of the lumbo-sacral region of a human spine, into which a pair of intervertebral spacers of the type shown in FIGS. 3–5 have been implanted.

Referring now to FIG. 6, the implantation of the present device 170 is set forth hereinbelow. The implantation procedure begins with the removal the degenerated disc material (disc material 156 from the intervertebral space between L5 and L4 being shown) from the intervertebral space 162 between the vertebral bodies L5 and S1. This is followed by the preparation of the lower surface 158 of the upper vertebral body L5, and the upper surface 160 of the lower vertebral body S1. These bones are manually spread apart (distracted) to their proper spacing to achieve the desirable effect of alleviating pain and/or neurological disfunction associated with compression against surrounding nerves. The surfaces 158 and 160 are thereby prepared and positioned for the introduction of a pair of devices 170.

Each device 170 is introduced into the intervertebral space 162 in its initial disposition, with the exterior surfaces 112,114 parallel, transverse to the axis of the spine. The pair are laterally spaced apart from one another with their hinged ends 106 each directed posteriorly. The distracted bones L5 and S1 are spaced apart such that the posterior separation of the surfaces 158 and 160 is narrower than the posterior spacing. The distal (hinged) ends 106 are inserted until they are wedged between the surfaces 158,160.

In this position, the device 170 is in contact (and thereby providing support for the spinal column) only at the posterior surface points where the spacing is equal to the unexpanded thickness of the device. The threaded shafts 124 are then rotated to cause the corresponding nuts 134 to translate anteriorly thereby causing the proximal end 122 of the device 170 to spread.

In an alternative embodiment, the direction of the taper of the interior surfaces 116,118 of the opposing elements 100,102, and the corresponding direction of axial translation of the nut 134 may be reversed so that the movement of the nut 134 toward the distal, hinged, end 120 causes the proximal end 122 to expand.

Figure 7:
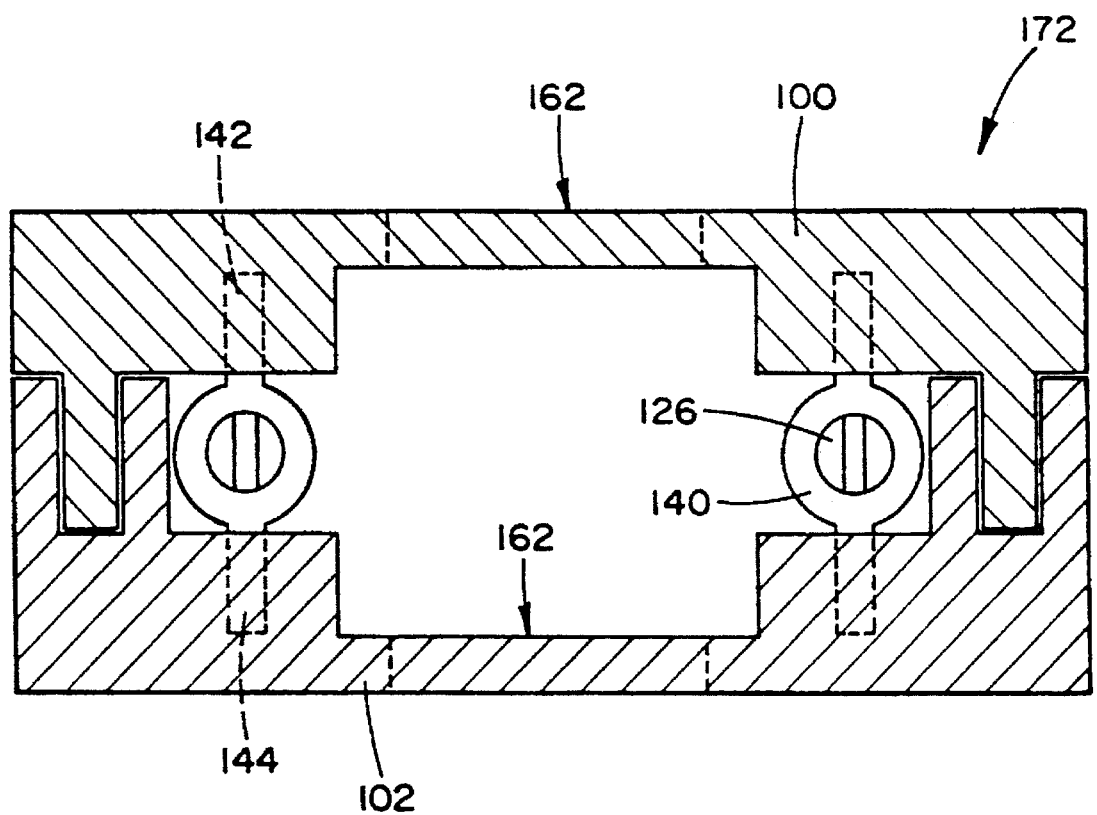
FIG. 7 is a front perspective view of another aspect of the present invention wherein dual shape altering means are included.
Figure 8:
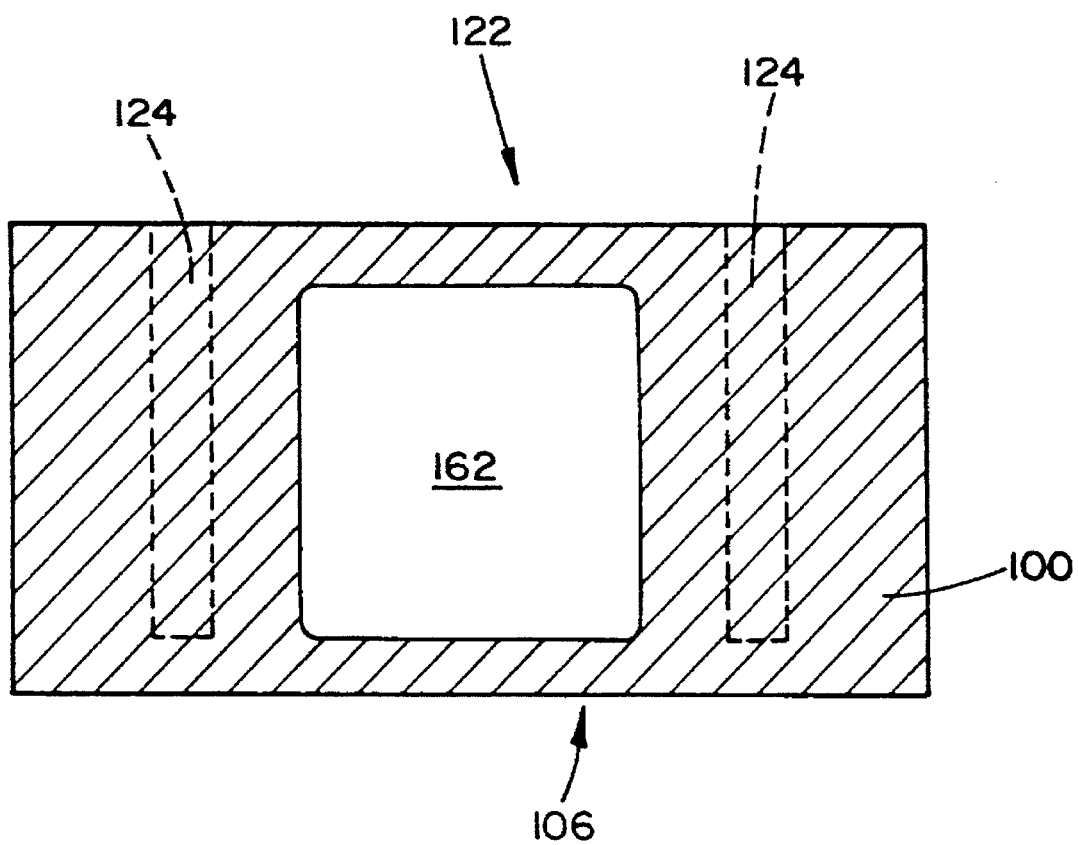
FIG. 8 is a top perspective view of the aspect of the present invention which is shown in FIG. 7.
Figure 9:
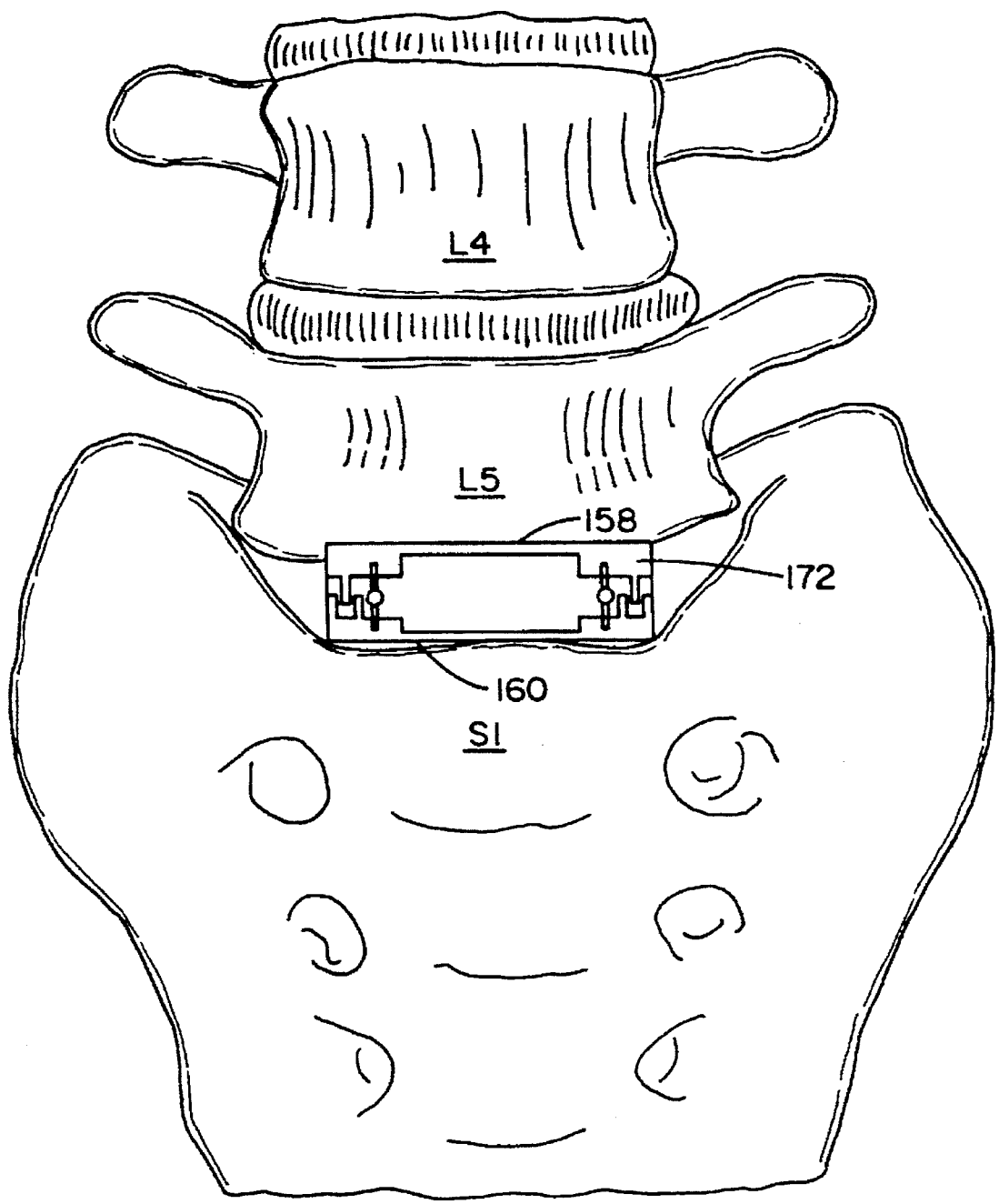
FIG. 9 is a front view of the anterior portion of the lumbo-sacral region of a human spine, into which an intervertebral spacer of the type shown in FIGS. 7 and 8 has been implanted.

With reference to FIGS. 7, 8, and 9, in which front, top, and implant views of an alternative embodiment of the present invention are provided, a device 172 may be constructed having a plurality of nut 134 and shaft 124 expansion means (either the distally or proximally directed ones) may be included in a single device 172 so that only one device need be implanted. In such a device, the opposing elements 100,102 preferably include holes 162, or a single through hole, through which bone may grow across the intervertebral space. In addition, it is possible to rotationally offset the device 172 in the plane transverse to the axis of the spine to correspond to malformation of the vertebral body.

While there has been described and illustrated implantation devices for stabilizing and immobilizing regions of the spine by inserting a shape conforming cage in the intervertebral space between adjacent vertebral bodies, it will be apparent to those skilled in the art that variations and modifications are possible without deviating from the broad spirit and principle of the present invention which shall be limited solely by the scope of the claims appended hereto.

We claim:

1. A shape conforming implant device for positioning in an intervertebral space, said device comprising:

first and second cupping elements, each of said cupping elements having concave inner surfaces, said concave inner surfaces facing one another thereby defining an interior volume therebetween, said cupping elements being coupled together by a hinge at a first end thereof, and defining an opening at a second end thereof, said interior volume having first and second regions thereof which correspond to said first and second ends of said cupping elements;

said concave inner surfaces further being tapered such that the interior volume has an axial taper such that one of the first and second regions of said interior volume is greater than the other of the first and second regions of said interior volume;

a threaded shaft disposed between said first and second cupping elements;

a nut, disposed on said threaded shaft, said nut having a radial dimension which places it in contact with said inner surfaces such that rotation of the threaded shaft causes the translation of the nut within the axially tapered interior volume, such translation along the tapered inner surfaces causing the first and second cupping elements to swing about said hinge and spread such that the device is conformable to the shape of the intervertebral space; and a retaining ring, disposed within said opening at said second end, through which the threaded shaft is disposed, and by which the threaded shaft is retained within the interior volume.

2. The shape conforming implant device as set forth in claim 1, wherein said threaded shaft is coaxially disposed within said interior volume.

3. The shape conforming implant device as set forth in claim 1, said cupping elements further comprising planar outer surfaces.

4. The shape conforming implant device as set forth in claim 3, wherein said planar outer surfaces of said cupping elements further include an efficacious conformation for gripping bone surfaces.

5. The shape conforming implant device as set forth in claim 1, wherein said concave inner surfaces are tapered such that the first region of said interior volume is greater than the second region thereof, and correspondingly the concave inner surfaces of each of said first and second cupping elements are disposed more closely to one another at the second end than at the first end, whereby the cupping elements spread apart by translation of the nut toward the second end.

6. The shape conforming implant device as set forth in claim 1, wherein said concave inner surfaces are tapered such that the second region of said interior volume is greater than the first region thereof and correspondingly the concave inner surfaces of each of said first and second cupping elements are disposed more closely to one another at the first end than at the second end, whereby the cupping elements spread apart by translation of the nut toward the first end.

7. A shape conforming implant device for positioning in an intervertebral space, said device comprising:

first and second cupping elements, each of said cupping elements having concave inner surfaces, said concave inner surfaces facing one another thereby defining an interior volume therebetween, said cupping elements being coupled together by a hinge at a first end thereof, and defining an opening at a second end thereof, said interior volume having first and second regions thereof which correspond to said first and second ends of said cupping elements;

said concave inner surfaces further being tapered such that the interior volume has an axial taper such that one of the first and second regions of said interior volume is greater then the other of the first and second regions of said interior volume;

a plurality of threaded shafts disposed in parallel between said first and second cupping elements;

a corresponding plurality of nuts, disposed on said threaded shafts, said nuts having a radial dimension which places them in contact with said concave inner surfaces such that rotation of respective threaded shafts causes the translation of the nuts within the axially tapered interior volume, such translation along the tapered inner surfaces causing the first and second cupping elements to swing about said hinge and spread such that the device is conformable to the shape of the intervertebral space.

8. The shape conforming implant device as set forth in claim 7, wherein said cupping elements are perforate.

9. A shape conforming implant device for positioning in an intervertebral space, said device comprising;

first and second cupping elements, each of said cupping elements having first and second ends and concave inner surfaces, said concave inner surfaces facing one another thereby defining an interior volume therebetween, said cupping elements being coupled together by a hinge at said first ends thereof;

means for selectively causing the first and second cupping elements to rotate relative to one another about said hinge, thereby expanding the interior volume and causing the device to conform to the shape of the intervertebral space.

\* \* \* \* \*